United States Patent
Eberhardt et al.

(10) Patent No.: US 10,407,385 B2
(45) Date of Patent: Sep. 10, 2019

(54) UREAURETHANES FOR RHEOLOGY CONTROL

(71) Applicant: BYK-Chemie, GmbH, Wesel (DE)

(72) Inventors: Marc Eberhardt, Wesel (DE); René Nagelsdiek, Hamminkeln (DE); Sylvia Bühne, Duisburg (DE); Jürgen Omeis, Dorsten-Lembeck (DE); Agnetha Schmitt, Gelsenkirchen (DE)

(73) Assignee: BYK-Chemie GmbH, Wesel (DE)

( * ) Notice: Subject to any disclaimer, the term of this patent is extended or adjusted under 35 U.S.C. 154(b) by 0 days.

(21) Appl. No.: 15/577,970

(22) PCT Filed: Jul. 22, 2016

(86) PCT No.: PCT/EP2016/067588
§ 371 (c)(1),
(2) Date: Nov. 29, 2017

(87) PCT Pub. No.: WO2017/017036
PCT Pub. Date: Feb. 2, 2017

(65) Prior Publication Data
US 2018/0170860 A1    Jun. 21, 2018

(30) Foreign Application Priority Data
Jul. 27, 2015 (EP) ................................ 15178541

(51) Int. Cl.
| | | |
|---|---|---|
| *C08G 18/76* | (2006.01) | |
| *C08G 18/81* | (2006.01) | |
| *C07C 275/40* | (2006.01) | |
| *C08G 18/67* | (2006.01) | |
| *C08L 75/16* | (2006.01) | |
| *C07C 273/18* | (2006.01) | |
| *C07C 275/26* | (2006.01) | |
| *C09D 5/04* | (2006.01) | |
| *C08G 18/32* | (2006.01) | |
| *C08L 75/04* | (2006.01) | |
| *C09D 7/45* | (2018.01) | |
| *G01N 30/00* | (2006.01) | |

(52) U.S. Cl.
CPC .......... *C07C 275/40* (2013.01); *C07C 273/18* (2013.01); *C07C 275/26* (2013.01); *C08G 18/324* (2013.01); *C08G 18/675* (2013.01); *C08G 18/6715* (2013.01); *C08G 18/7621* (2013.01); *C08G 18/8166* (2013.01); *C08L 75/04* (2013.01); *C08L 75/16* (2013.01); *C09D 5/04* (2013.01); *C09D 7/45* (2018.01); *G01N 2030/486* (2013.01)

(58) Field of Classification Search
CPC ... C07C 275/40; C07C 275/26; C07C 275/28; C07C 273/18; C08G 18/324; C08G 18/6715; C08G 18/675; C08G 18/7621; C08G 18/8166; C08L 75/04; C08L 75/16
See application file for complete search history.

(56) References Cited

U.S. PATENT DOCUMENTS

2002/0115882 A1    8/2002  Haubennestel et al.
2012/0226075 A1    9/2012  Leutfeld et al.

FOREIGN PATENT DOCUMENTS

EP         2292675 A1     3/2011

OTHER PUBLICATIONS

PCT/EP2016/067588—International Search Report, dated Oct. 26, 2016.
PCT/EP2016/067588—International Written Opinion, dated Oct. 26, 2016.

*Primary Examiner* — Michael L Leonard
(74) *Attorney, Agent, or Firm* — Curatolo Sidoti Co., LPA; Joseph G. Curatolo; Salvatore A. Sidoti

(57) ABSTRACT

The present invention relates to ureaurethanes of the following formula (I)

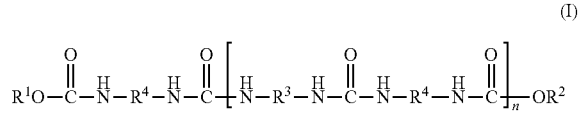

in which at least one of the $R^1$ or $R^2$ radicals is a mono- or polyunsaturated, branched or unbranched alkenyl or alkynyl radical having 12 to 24 carbon atoms, n is an integer ≥1, where the upper limit for n arises from the maximum number average molecular weight $M_n$ of the ureaurethanes of the general formula (I), which is 65 000 g/mol, and which is determined by means of gel permeation chromatography to DIN 55672-2 using a polymethyl methacrylate standard, $R^3$ is a xylylene radical or a hydrogenated xylylene radical and $R^4$ is a tolylene radical or various other radicals. The invention also relates to ureaurethane compositions comprising the ureaurethanes of the invention and to the preparation of both. The invention further relates to the use of the ureaurethanes or ureaurethane compositions as rheology control agent and antisettling agent. The invention further provides liquid formulations from the group consisting of coating compositions, polymer formulations, pigment pastes, sealant formulations, cosmetics, ceramic formulations, drilling fluids, adhesive formulations, potting compounds, construction material formulations, lubricants, spackling compounds, printing inks and other inks, comprising the ureaurethanes and ureaurethane compositions.

21 Claims, No Drawings

UREAURETHANES FOR RHEOLOGY CONTROL

CROSS REFERENCE TO RELATED APPLICATIONS

This application is a national stage application of International Application No. PCT/EP2016/067588, filed 22 Jul. 2016, which claims priority from European Patent Application No. 15178541.7, filed 27 Jul. 2015, which applications are incorporated herein by reference.

The present invention relates to urea urethanes and to the use thereof and formulations comprising them, to the production and use thereof, and to liquid formulations comprising them.

BACKGROUND OF THE INVENTION

In order to control the rheology of liquid systems, especially liquid coating systems or drilling fluid solutions, rheological auxiliaries used are predominantly organically modified bentonites, silicas, hydrogenated castor oil and polyamide waxes.

A disadvantage of the use of these rheological auxiliaries is that they are usually in the form of dry solids. Consequently, therefore, said rheological auxiliaries are digested prior to use to give an intermediate product using solvents and shear forces. Alternatively, the as yet undigested rheological auxiliaries can also be used by introducing them into the liquid system via specific temperature control. If this temperature control does not follow the specifications, there is typically occurrence of crystallites in the finished coating system that can lead to defects in the coating.

A general drawback of the use of these rheological auxiliaries is that they cause cloudiness and haze in clear transparent coatings. Moreover, it is undesirable to work with dry pulverulent products that can cause dusts in processing.

A liquid use alternative to these solid rheology control agents is that of solutions of specific urea compounds.

Solutions of this kind are frequently used in practice and are described, for example, in the laid-open document DE 2822908, in EP-B1-0006252, in DE-A1-19919482, in EP-A1-1188779 and in EP-A-2370489.

Solvents or carrier media used are typically polar aprotic solvents and/or what are called ionic liquids, which are in fact salt melts that are liquid under moderate temperature conditions (usually below 80° C., ideally at room temperature).

The rheology control properties of dissolved urea compounds are usually quite good, but in many cases there is a need for optimization with regard to the storage stability of corresponding urea solutions; in other words, the solution of the urea should not form any precipitates as a result of premature urea crystallization. In practice, this means that a solution of the urea can readily be stored and transported and hence use as a rheological control agent (for example on the part of a paint manufacturer) is possible within a sufficient time window after the actual production of the rheology control agent.

There is further need for optimization with regard to the spectrum of action as a rheology control agent; in other words, there is a need for rheology control agents which enable usability in systems of particularly low polarity in which the known urea compounds are not usable with a satisfactory outcome. Thus, optimized behavior of urea-based rheology control agents is manifested not just in basically improved rheological efficacy but also in compatibility and simultaneously good efficacy in particularly non-polar application-relevant formulations (for example specific binder systems, purge solutions or other liquid media), preferably with simultaneously excellent storage stability of the corresponding compositions used as rheology control agents.

Laid-open specification DE 2822908 describes thixotropic agents comprising linear urea urethanes bearing alkyl groups and/or alkyl-terminated (poly)alkylene oxide groups as end groups.

EP-B1-0006252 describes a process for producing thixotropic agents in the presence of an aprotic solvent and lithium chloride. The thixotropic agents obtained have the end groups already described in laid-open specification DE 2822908.

DE-A1-19919482 discloses a further development of the process described in EP-B1-0006252, in that specifically monoisocyanate adducts are prepared from diisocyanates and monoalcohols, in order then to react them with diamines in the presence of lithium salts and aprotic solvents. The urea urethanes described in DE-A1-19919482 also contain exclusively saturated end groups optionally containing heteroatoms, or aralkyl groups as end groups. A typical representative of the urea urethanes known from DE-A1-19919482 is obtained in example 12 therein and is based on a monoadduct of one molecule of n-dodecanol onto one molecule of tolylene diisocyanate, which is then reacted with xylylenediamine to give the end product. EP-A1-2370489 presents a further development of the process in which it is possible to dispense with lithium salts, and ionic liquids, i.e. liquid organic salts, are used.

EP-A1-1188779 focuses on urea urethanes as rheology control agents suitable for imparting thixotropy to formulations containing primarily water or water and small amounts of polar organic solvents. It is essential to the invention in EP-A1-1188779 that the end groups of the urea urethanes must necessarily be different than one another. All the examples of EP-A1-1188779 disclose urea urethanes in which at least one of the two end groups is an end group derived from butyltriglycol and/or methoxy polyethylene glycol. Only in examples 8 and 13 are urea urethane solutions prepared that have not only a butyltriglycol-derived end group but also a nonpolar end group, namely an isotridecyl group (derived from isotridecanol).

EP-A1-2292675 in turn describes polymeric ureas which may bear saturated or unsaturated hydrocarbyl groups bonded via urea or urethane groups, or a multitude of different groups which also contain heteroatoms such as oxygen and nitrogen, as end groups. Although example 5 also describes a product oleyl-terminated at both ends, it is obtained using isophorone diisocyanate and hexamethylenediamine.

DE 101 27 290 A1 describes thixotropic unsaturated polyester resin compositions. The thixotropic agents used therein are generally prepared in the presence of the polyester resin. For the preparation, adducts of aliphatic isocyanates and olefinically unsaturated hydroxyl compounds are first prepared, and these are then reacted with aliphatic or araliphatic amines in the polyester resin, optionally also with further reaction with the polyester resin itself. The only olefinically unsaturated hydroxyl compounds specified explicitly are hydroxy (meth)acrylates, which serve for incorporation into the polyester resin at a later stage, in order to display their full effect therein. However, the results in relation to the thixotropic effect of the thixotropic agents of DE 101 27 290 A1 suggest that the nature of the unsaturated polyester resin is of great significance. Unsaturated long-chain hydrocarbyl radicals as end groups of urea urethanes are not mentioned anywhere in DE 101 27 290 A1.

It is thus a particular object of the present invention to provide a correspondingly high-quality rheology control agent. This is to be superior, especially in nonpolar systems, to the known rheology control agents in terms of sagging characteristics on use in coating compositions and/or else is to improve the antisettling characteristics of solids in liquid formulations. Moreover, the adverse properties of the rheology control agents known from the prior art were to be overcome. These and further benefits described hereinafter are achieved through provision of the urea urethanes and urea urethane compositions described hereinafter.

Urea Urethanes

The object of the invention was especially achieved through provision of urea urethanes of the general formula (I)

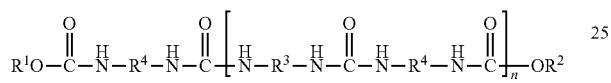

(I)

in which $R^1$ is a mono- or polyunsaturated, branched or unbranched alkenyl radical having 12 to 24 carbon atoms, a mono- or polyunsaturated, branched or unbranched alkynyl radical having 12 to 24 carbon atoms or a polyunsaturated hydrocarbyl radical which has 12 to 24 carbon atoms and has at least one carbon-carbon double bond and at least one carbon-carbon triple bond, $R^2$ is a saturated branched or unbranched alkyl radical having 8 to 24 carbon atoms or a mono- or polyunsaturated, branched or unbranched alkenyl radical having 12 to 24 carbon atoms, a mono- or polyunsaturated, branched or unbranched alkynyl radical having 12 to 24 carbon atoms or a polyunsaturated hydrocarbyl radical which has 12 to 24 carbon atoms and has at least one carbon-carbon double bond and at least one carbon-carbon triple bond, and all n $R^3$ radicals are independently one or more radicals selected from the structural units (IIa-o), (IIa-m), (IIa-p), (IIb-o), (IIb-m) and (IIb-p)

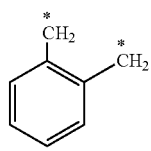

(IIa-o)

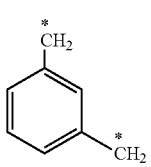

(IIa-m)

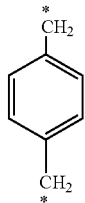

(IIa-p)

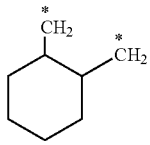

(IIb-o)

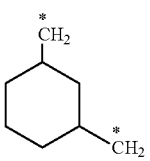

(IIb-m)

(IIb-p)

and all n+1 $R^4$ radicals are independently one or more radicals selected from the structural units (IIIa), (IIIb), (IIIc), (IIId), (IIIe), (IIIf), (IIIg) and (IIIh)

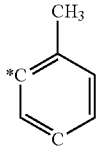

(IIIa)

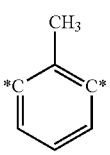

(IIIb)

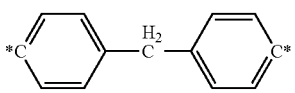

(IIIc)

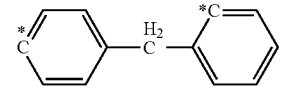

(IIId)

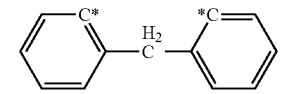

(IIIe)

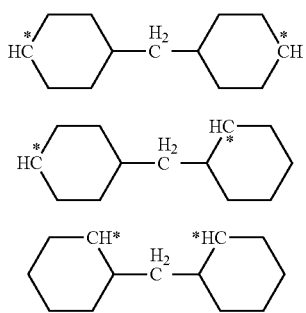

and n is an integer ≥1, where the upper limit for n arises from the maximum number-average molecular weight $M_n$ of the urea urethanes of the general formula (I) which is 65 000 g/mol and which is determined by means of gel permeation chromatography to DIN 55672-2 using a polymethylmethacrylate standard.

In this context, a specific figure for a maximum value of "n" is unnecessary since it is limited by the fixed upper limit of $M_n$. What is thus symbolized by "n" is merely that the urea urethanes may be oligomers or polymers when n 1, containing n [NH—$R^3$—NH—CO—NH—$R^4$—NH—CO] units.

Typically, n is an integer from 1 to 150 or 1 to 125, preferably 1 to 100 or 1 to 75 and most preferably 1 to 50 or 1 to 25. In addition, preference is given to values of n=1 to 15, 1 to 10 and 1 to 5.

When n=1, the urea urethanes take the form of compounds having a specific molecular weight. These compounds are particularly preferred herein.

However, the urea urethanes may also be oligomeric or polymeric, meaning that, if n≥2, there may be molecular inhomogeneity; in such cases, these have a weight-average and a number-average molecular weight, where these average values can generally differ from one another to a greater degree with increasing n.

The number-average molar masses of the urea urethanes up to about 1000 g/mol can be determined by means of NMR, for example, by determining the ratios of the integrals of NMR resonance signals in question. The person of average skill in the art is aware that, for higher molecular weight ranges, other processes are preferable rather than NMR spectroscopy for determination of the molecular weights. The number-average molecular weight of the urea urethanes having a molar mass of more than 1000 g/mol is determined in accordance with the description which follows as the number average of the molar mass distribution determined by means of gel permeation chromatography (GPC). The GPC molar mass distribution is determined according to DIN 55672 Part 2 of June 2008. The eluent used is a solution of lithium bromide (content: 5 g/L) in dimethylacetamide. Calibration is accomplished using polymethylmethacrylate standards having narrow distribution and a linear structure and having molecular weights between 1 000 000 and 102 g/mol. The temperature of the column system is 50° C.

On the basis of the smallest $R^2$, $R^3$ and $R^4$ radicals in terms of their molecular weight, when n=1, there is a theoretical lower limit in the molecular weight of the urea urethanes of the general formula (I) of 794 g/mol when a trialkenically unsaturated hydrocarbyl radical having 12 carbon atoms is used as $R^1$, or of 792 g/mol when a dialkynically unsaturated hydrocarbyl radical is used as $R^1$, or of 798 g/mol when a monoalkenically unsaturated hydrocarbyl radical is used as $R^1$, or of 796 g/mol when a monoalkynically unsaturated hydrocarbyl radical is used as $R^1$. Since, when n=1, the compounds are homogeneous under the aforementioned conditions, it is the molecular weight and not the number-average molecular weight $M_n$ or weight-average molecular weight $M_w$ that is typically referred to, since, in the case of molecular homogeneity, the molecular weight=$M_n$=$M_w$ and the manner in which the average is formed is unimportant.

According to the invention, the upper limit in the number average molecular weight $M_n$ of the inventive urea urethanes of the general formula (I) is 65 000 g/mol, preferably 50 000 g/mol or 30 000 g/mol, more preferably 20 000 g/mol or 10 000 g/mol and most preferably 6000 g/mol, 5000 g/mol or 4000 g/mol.

The bonding sites of the $R^3$ and $R^4$ radicals to the adjacent NH groups in the above formulae are indicated by the * symbol.

Even though no particular definition is required, the terms "alkyl radical", "alkenyl radical" and "alkynyl radical" herein, in accordance with the standard chemical nomenclature, are regarded as being particular embodiments of aliphatic hydrocarbyl radicals. They are thus radicals which, in accordance with the IUPAC definition of a hydrocarbon, contain exclusively carbon and hydrogen atoms and are thus free of heteroatoms, for example oxygen or nitrogen.

The urea urethanes shown above are referred to hereinafter as urea urethanes of the invention.

Urea Urethane Compositions

The invention further provides urea urethane compositions comprising the urea urethanes of the invention, wherein the proportion by weight of the urea urethanes of the formula (I) in which both $R^1$ and $R^2$ radicals are unsaturated is 10% to 100%, based on the totality of the urea urethanes of the formula (I), and the proportion by weight of the urea urethanes of the formula (I) in which only one of the $R^1$ radicals is unsaturated is 0% to 90%, based on the totality of the urea urethanes of the formula (I).

The aforementioned urea urethane compositions are also referred to herein as urea urethane compositions of the invention.

The urea urethane compositions of the invention may, as well as the inventive urea urethanes of the formula (I), additionally also comprise urea urethanes other than these. Such urea urethanes other than the urea urethanes of the invention may, for example, be urea urethanes bearing the $R^1$, $R^3$ and $R^4$ radicals as defined in accordance with the invention and containing an $R^2$ radical that differs from the $R^2$ radicals of the invention in that it contains a smaller or greater number of carbon atoms and/or contains oxygen atoms and hence is not a hydrocarbyl radical. A radical of this kind could, for example, contain one or more ether oxygen atoms, as is the case, for example, in a di-, tri- or tetraethylene glycol monobutyl ether radical. If noninventive urea urethanes of this kind are present in the urea urethane compositions of the invention, these can be introduced subsequently into the urea urethane compositions of the invention or else form in situ. The latter is possible, for example, when small amounts of the monoadducts of diisocyanate and noninventive alcohol are present in the reaction of the monoadducts usable in accordance with the invention with the diamines usable in accordance with the invention.

In a preferred embodiment, however, at least 50% by weight of all urea urethanes in the urea urethane composition have a structure (I). More preferably, at least 50% by weight of all urea urethanes in the urea urethane composition have a structure (I) in which both $R^1$ and $R^2$ are unsaturated, preferably ethylenically unsaturated.

In a further preferred embodiment of the urea urethane compositions of the invention, the proportion by weight of the urea urethanes of the formula (I) in which both $R^1$ and $R^2$ radicals are unsaturated is 20% to 100%, based on the totality of the urea urethanes of the formula (I), and the proportion by weight of the urea urethanes of the formula (I) in which only the $R^1$ radical is unsaturated is 0% to 80%, based on the totality of the urea urethanes of the formula (I).

In a preferred embodiment of the urea urethane compositions of the invention, the proportion by weight of the urea urethanes of the formula (I) in which both $R^1$ and $R^2$ radicals are unsaturated is 50% to 100%, based on the totality of the urea urethanes of the formula (I), and the proportion by weight of the urea urethanes of the formula (I) in which only the $R^1$ radical is unsaturated is 0% to 50%, based on the totality of the urea urethanes of the formula (I).

In a preferred embodiment of the urea urethane compositions of the invention, the proportion by weight of the urea urethanes of the formula (I) in which both $R^1$ and $R^2$ radicals are unsaturated is 70% to 100%, based on the totality of the urea urethanes of the formula (I), and the proportion by weight of the urea urethanes of the formula (I) in which only the $R^1$ radical is unsaturated is 0% to 30%, based on the totality of the urea urethanes of the formula (I).

In a preferred embodiment of the urea urethane compositions of the invention, the proportion by weight of the urea urethanes of the formula (I) in which both $R^1$ and $R^2$ radicals are unsaturated is 80% to 100%, based on the totality of the urea urethanes of the formula (I), and the proportion by weight of the urea urethanes of the formula (I) in which only the $R^1$ radical is unsaturated is 0% to 20%, based on the totality of the urea urethanes of the formula (I).

In a preferred embodiment of the urea urethane compositions of the invention, the proportion by weight of the urea urethanes of the formula (I) in which both $R^1$ and $R^2$ radicals are unsaturated is 90% to 100%, based on the totality of the urea urethanes of the formula (I), and the proportion by weight of the urea urethanes of the formula (I) in which only the $R^1$ radical is unsaturated is 0% to 10%, based on the totality of the urea urethanes of the formula (I).

In a further embodiment, the urea urethane compositions of the invention contain 100% urea urethanes of the formula (I) in which both $R^1$ and $R^2$ radicals are unsaturated, preferably ethylenically unsaturated, based on the totality of the urea urethanes of the formula (I).

In a preferred embodiment of the urea urethanes of the invention and of the urea urethane compositions of the invention that comprise them, the $R^1$ radical is a mono- or polyunsaturated, branched or unbranched alkenyl radical having 12 to 20 carbon atoms, the $R^2$ radical is a saturated branched or unbranched alkyl radical having 8 to 20 carbon atoms or a mono- or polyunsaturated, branched or unbranched alkenyl radical having 12 to 20 carbon atoms, the n $R^3$ radicals are independently one or more radicals selected from the structural units (IIa-m) and (IIa-p), and the n+1 $R^4$ radicals are independently one or more radicals of the structural units (IIIa) and (IIIb).

In a particularly preferred embodiment of the urea urethanes of the invention and of the urea urethane compositions of the invention that comprise them, the $R^1$ radical is a monounsaturated alkenyl radical having 16 to 20 carbon atoms, the $R^2$ radical is a saturated branched alkyl radical having 10 to 16 carbon atoms or a monounsaturated alkenyl radical having 16 to 20 carbon atoms, the n $R^3$ radicals are independently one or more radicals selected from the structural units (IIa-m) and (IIa-p), and the n+1 $R^4$ radicals are independently one or more radicals of the structural units (IIIa) and (IIIb).

In a very particularly preferred embodiment of the urea urethanes of the invention and of the urea urethane compositions of the invention that comprise them, the $R^1$ radical is an unbranched octadecenyl radical, preferably an oleyl radical, the $R^2$ radical is a branched or unbranched $C_{10}$-$C_{14}$ radical, preferably an isotridecyl radical, or an unbranched octadecenyl radical, preferably an oleyl radical, the n $R^3$ radicals are a radical of the structural unit (IIa-m), and the n+1 $R^4$ radicals are independently one or more radicals of the structural units (IIIa) and (IIIb).

For all embodiments of the urea urethanes of the invention and of the urea urethane compositions that comprise them, the structural units (IIIa) and (IIIb) are preferably present in the n+1 $R^4$ radicals in a molar ratio of 40:60 up to a molar ratio of 100:0; even more preferably, the structural units (IIIa) and (IIIb) are present in the n+1 $R^4$ radicals in a molar ratio of 50:50 up to a molar ratio of 100:0; and most preferably, the structural units (IIIa) and (IIIb) are present in the n+1 $R^4$ radicals in a molar ratio of 60:40 up to a molar ratio of 100:0.

For embodiments of the urea urethanes of the invention and of the urea urethane compositions of the invention that comprise them, it is preferably the case that $R^1$ and $R^2$ are a mono- or polyunsaturated, more preferably monounsaturated, branched or unbranched, more preferably unbranched, alkenyl radical having 12 to 20 and more preferably 16 to 20 carbon atoms. More preferably, for all embodiments, $R^1$=$R^2$; most preferably, $R^1$=$R^2$=oleyl.

For practical applicability, it is appropriate to provide the urea urethane compositions of the invention in liquid form, preferably in liquid form under application conditions, more preferably in liquid form at room temperature, i.e. at 25° C. Preferably, the urea urethanes of the invention are in dissolved form in the urea urethane compositions of the invention at room temperature.

Suitable solvents are especially aprotic organic solvents. Particularly suitable solvents are polar aprotic organic solvents, most preferably those that are selected from the group of the amides, lactams, sulfoxides and ionic liquids (i.e. organic salts having a melting point of ≤80° C.). It is therefore preferable to conduct the preparation of corresponding urea urethane compositions of the invention in these polar aprotic organic solvents or ionic liquids.

Particularly preferred polar aprotic organic solvents here are substituted or to unsubstituted, preferably unsubstituted, N-alkylpyrrolidones, dialkyl sulfoxides, substituted or unsubstituted amides, especially carboxamides. Examples of N-alkylpyrrolidones are N-methylpyrrolidone, N-ethylpyrrolidone, N-octylpyrrolidone and N-hydroxyethylpyrrolidone. One example of a dialkyl sulfoxide is dimethyl sulfoxide. Examples of amides are N,N-dimethylformamide, N,N-dimethylacetamide, N,N-dialkylamido alkyl esters, N,N-dialkylamido alkyl ethers, hexamethylphosphoramide and acylmorpholines. Preferred ionic liquids that are suitable as solvents are substituted imidazolium salts, for example 1-ethyl-3-methylimidazolium acetate, 1-ethyl-3-methylimidazolium acetate, 1-ethyl-3-methylimidazolium ethylsulfate, 1-butyl-3-methylimidazolium ethylsulfate, 1-ethyl-3-methylimidazolium thiocyanate and 1-butyl-3-methylimidazolium thiocyanate. Corresponding solvents can also be used in combinations.

Among the solvents, preference is given to dimethyl sulfoxide and especially those N-alkylpyrrolidones wherein the nitrogen-bonded alkyl radical is linear or branched, preferably linear, and the alkyl radical contains 1 to 20 or preferably 2 to 20, more preferably 3 to 16 and most preferably 4 to 12 carbon atoms, and also N,N-dimethylamido alkyl esters, N,N-dimethylamido alkyl ethers, formylmorpholine and acetylmorpholine.

In order to improve the dissolution properties of the solvents, salts, i.e. ionogenic compounds, are frequently also added. These are preferably salts of cations of main groups I and II of the Periodic Table of the Elements (alkali metals and alkaline earth metals) or ammonium salts, preferably lithium, calcium or magnesium salts, more preferably lithium or calcium salts. Preferred anions are monovalent anions, more preferably halide, pseudohalide, formate, acetate and/or nitrate, most preferably chloride, acetate and/or nitrate.

Preparation of the Urea Urethanes of the Invention and of the Urea Urethane Compositions of the Invention The urea urethane composition of the invention can be prepared in a known manner by reacting corresponding isocyanates with amines. Preparation processes for urea urethanes of this kind are described in detail, for example, in EP-B1-0006252, DE 2822908, DE 19919482, EP 1188779 and EP-A1-2370489. Preferably, the preparation of the urea urethane composition also takes place by these aforementioned preparation processes.

Preferred urea urethane compositions are therefore those in which the composition has been obtained by such a preparation process.

For example, it is first possible to prepare one or more monoadducts from one or more monoalcohols of the structures $R^1OH$ and/or $R^2OH$ and one or more diisocyanates $OCN-R^4-NCO$, which results in monoadducts of the formula $R^1-O-(CO)-NH-R^4-NCO$ or $R^2-O-(CO)-NH-R^4-NCO$ as adducts. These monoadducts can be obtained, for example, using an excess of diisocyanate, in which case, after preparation thereof, the excess diisocyanate can be removed, for example by distillation.

The monoadducts can then be reacted with one or more diamines of the structure $H_2N-R^3-NH_2$ to give the end product.

Rather than the aforementioned diamines, it is also possible to use one or more prepolymers, $NH_2$-terminated at both ends, of one or more of the aforementioned diamines and one or more of the aforementioned diisocyanates. Subsequently, the prepolymer(s) is/are reacted with the monoadduct.

In a further illustrative embodiment, the monoadduct(s) is/are reacted in a one-pot reaction with a mixture of the diamine(s) of the structure $H_2N-R^3-NH_2$ and one or more diisocyanates $OCN-R^4-NCO$ to give the urea urethane (I).

In a further alternative, the monoadduct(s) is/are reacted with one or more prepolymers $NH_2$-terminated at both ends or a mixture of one or more diamines of the structure $H_2N-R^3-NH_2$ and one or more prepolymers $NH_2$-terminated at both ends, and also one or more diisocyanates of the formula $OCN-R^4-NCO$ to give the urea urethane (I).

It is also possible to use a diisocyanate $OCN-R^4-NCO$ and a diamine $H_2N-R^3-NH_2$ to prepare a prepolymer NCO-terminated at both ends, and to react this prepolymer with monoalcohols of the structures $R^1OH$ and/or $R^2OH$ in order to arrive at the urea urethanes of the present invention.

In all the aforementioned cases, however, it is necessary for at least one monoalcohol of the formula $R^1OH$ to be used.

The reactions preferably take place in the aforementioned polar aprotic solvents. Urea urethanes themselves can, if desired, be obtained for example by distillative removal of the solvents.

Fields of Use of the Urea Urethanes of the Invention and of the Urea Urethane Compositions of the Invention The urea urethanes of the invention and the urea urethane compositions that comprise them exhibit particularly good rheological efficacy in nonpolar binder systems, for example long oil alkyds, medium oil alkyds, NAD (nonaqueous dispersion) systems, TPA (thermoplastic acrylate) systems. The rheological efficacy of the composition can be determined, for example, from the sag resistance, i.e. the sagging limit, of a corresponding paint formulation.

Surprisingly, the urea urethanes of the invention or the urea urethane compositions of the invention that comprise them can also be used in formulations that are low in organic binders or even free of organic binders, for example in what are called drilling fluid solutions.

The urea urethanes of the invention and the urea urethane compositions that comprise them are therefore preferably rheology control agents, more preferably thixotropic agents, each of which likewise form part of the subject matter of the present invention.

A further field of use of the urea urethanes of the invention and of the urea urethane compositions that comprise them is that of use as an antisettling agent, i.e. as an additive that delays or even prevents the sedimentation of solid particles in liquid systems; these particles here may be either inorganic or organic in nature. Examples of useful corresponding systems include paint, adhesive, lubricant and polymer formulations, and also drilling fluid solutions (frequently in the form of W/O emulsions in which the continuous phase is a hydrocarbon and the disperse phase is aqueous) and nonaqueous slurries (for example slurries of guar or xanthan in a hydrocarbon), as used in gas and oil production.

The urea urethane compositions of the invention additionally exhibit marked compatibility in nonpolar systems in particular, meaning that formation of specks, haze and/or cloudiness in such formulations, for example coating compositions, especially those based on nonpolar solvents, is reduced or ideally entirely eliminated compared to the alternatives known from the prior art.

At the same time, solutions of the composition of the invention have excellent storage stability, meaning that no crystallization of the urea urethanes takes place over extended periods of time in suitable solvents, which can also be used in combination.

Preferred solvents here are substituted or unsubstituted, preferably unsubstituted, N-alkylpyrrolidones, dialkyl sulfoxides, substituted or unsubstituted amides, especially carboxamides. Examples of N-alkylpyrrolidones are N-methylpyrrolidone, N-ethylpyrrolidone, N-octylpyrrolidone and N-hydroxyethyl pyrrolidone. One example of a dialkyl sulfoxide is dimethyl sulfoxide. Examples of amides are N,N-dimethylformamide, N,N-dimethylacetamide, N,N-dialkylamido alkyl esters, N,N-dialkylamido alkyl ethers, hexamethylphosphoramide and acylmorpholines. Preferred ionic liquids that are suitable as solvents are substituted imidazolium salts, for example 1-ethyl-3-methylimidazolium acetate, 1-ethyl-3-methylimidazolium acetate, 1-ethyl-3-methylimidazolium ethylsulfate, 1-butyl-3-methylimidazolium ethylsulfate, 1-ethyl-3-methylimidazolium thiocyanate and 1-butyl-3-methylimidazolium thiocyanate.

Among the solvents, preference is given to dimethyl sulfoxide and especially those N-alkylpyrrolidones wherein the nitrogen-bonded alkyl radical is linear or branched, preferably linear, and preferably contains 1 to 20, more preferably 3 to 16 and most preferably 4 to 12 carbon atoms, and also N,N-dimethylamido alkyl esters, N,N-dimethylamido alkyl ethers, formylmorpholine and acetylmorpholine.

It is likewise possible to use various urea urethanes of the invention, urea urethane compositions of the invention, rheology control agents of the invention, thixotropic agents of the invention or antisettling agents of the invention in combination, i.e. a mixture of such substances, compositions or agents, preferably for rheology control, especially for imparting thixotropy, or as antisettling agents.

The present invention therefore further provides for the use of the urea urethanes of the invention or of the urea urethane compositions of the invention as antisettling agents or as rheology control agents, preferably as thixotropic agents, in each case in liquid formulations, preferably those that are liquid at room temperature (25° C.).

These liquid formulations are preferably coating compositions, for example paints and varnishes, or polymer formulations, pigment pastes, sealant formulations, cosmetics, ceramic formulations, drilling fluid solutions for gas and oil production, nonaqueous slurries, cleaning compositions, adhesive formulations, potting compounds, building material formulations, lubricants, spackling compounds, printing inks or other inks, for example inkjet inks.

Preferred liquid formulations are anhydrous or contain only small amounts of water. A small amount of water is understood herein to mean a water content of not more than 5% by weight, preferably not more than 2% by weight and more preferably not more than 1% by weight.

In a further particular embodiment, the liquid formulation forms the continuous phase of what is called a water-in-oil emulsion. The abovementioned amounts of water in that case relate solely to the liquid formulation present prior to the formation of the emulsion (i.e. the later "oil phase"). The proportion of water that merges from the aqueous phase into the continuous phase on formation of the emulsion is extremely small and is not taken into account here.

The water-in-oil emulsion, based on its total weight, may quite possibly have a water content of, for example, 20% or 30% by weight. Typical water-in-oil emulsions are what are called drilling muds, preferably oil drilling muds, which likewise form part of the subject matter of the present invention.

The paints and varnishes, printing inks and other inks, especially inkjet inks, may be either solventborne or solvent-free paints and varnishes, printing inks and other inks, such as inkjet inks. Paints and varnishes are usable in a wide variety of different fields of use, including in the field of automotive paint systems, architectural coatings, protective coatings (painting of ships and bridges inter alia), can and coil coatings, wood and furniture coatings, industrial coatings, polymer paint systems, wire coatings, coatings for food and drink and seed, and also what are called color resists which are used for color filters, for example in liquid-crystal displays. The field of use of paints and varnishes also includes pasty materials generally having a very high proportion of solids and a small proportion of liquid components, for example what are called pigment pastes or else pastes based on finely divided metal particles or metal powders (for example based on silver, copper, zinc, aluminum, bronze, brass). Pastes of this kind that comprise the urea urethanes or urea urethane compositions of the invention likewise form part of the subject matter of the present invention.

The polymer formulations are preferably liquid formulations, more preferably those that are liquid at room temperature, i.e. 25° C., for production of polymer materials which are preferably converted to a thermoset by a chemical crosslinking process ("curing"). Preferred polymer preparations are therefore unsaturated polyester resins, vinyl ester resins, acrylate resins, epoxy resins, polyurethane resins, formaldehyde resins (such as melamine-formaldehyde or urea-formaldehyde). These may be cured under a wide variety of different conditions, for example at room temperature (cold-curing systems) or at elevated temperature (hot-curing systems), optionally also with application of pressure ("closed-mold" application, sheet molding compounds or bulk molding compounds). The preferred polymer formulations also include PVC plastisols.

The cosmetic formulations may be manifold liquid compositions that are used in the personal care sector or else in the healthcare sector, for example lotions, creams, pastes, for example toothpaste, foams, for example shaving foams, gels, for example shaving gels, shower gels, medicaments formulated in gel form, hair shampoos, liquid soaps, nail varnishes, lipsticks or hair colorants.

The drilling fluid solutions are liquids which are pumped through the well in a drilling operation. In general, they are suspensions of solid inorganic particles that are frequently produced by means of a special mixer. They are preferably what are called oil-based drilling fluid solutions in which the continuous liquid phase consists of an organic liquid medium (generally a hydrocarbon) in which inorganic constituents such as barium sulfate are suspended, and which are frequently also in the form of an inverse emulsion, i.e. of an emulsion of water droplets in the organic medium. Likewise used with preference in gas and oil production are nonaqueous slurries, which are preferably suspensions of organic compounds, preferably polysaccharides (e.g. xanthan gum or guar gum), in hydrocarbons, which are often used as pumpable media with the aim of later thickening of aqueous media (for example in what is called hydraulic fracturing).

The lubricants are compositions which are used for lubrication, i.e. those which serve to reduce friction and wear, and for force transmission, cooling, vibration damping, sealing action and corrosion protection, preference being given here to liquid lubricants and lubricant greases.

The adhesives may be any process materials which are liquid under processing conditions and which can join adherends by virtue of areal bonding and internal strength. These adhesives may preferably be solvent-containing or solvent-free.

Finally, the present invention relates to the abovementioned liquid formulations comprising the urea urethanes of the invention or the urea urethane compositions of the invention.

The proportion of urea urethanes of the invention in the liquid formulations of the invention, especially the coating compositions, polymer formulations, pigment pastes, sealing formulations, cosmetics, ceramic formulations, nonaqueous slurries and drilling fluid solutions for gas and oil production, adhesive formulations, potting compounds, building material formulations, lubricants, spackling compounds, printing to inks or other inks, based on the total weight of the liquid formulation, is preferably 0.1% to 5% by weight, more preferably 0.15% to 3% by weight and most preferably 0.2% to 2.0% by weight.

Preferably, the liquid formulations of the invention additionally comprise one or more hydrocarbons selected from the group of the aliphatic, cycloaliphatic, aromatic and araliphatic hydrocarbons. More preferably, the hydrocarbon(s) is/are present in the liquid formulation to an extent of at least 10% by weight to 99% by weight based on the total weight of the liquid formulation. Preferred lower limits for the content of hydrocarbons in the liquid formulation are, for example, 15% or 20% by weight. However, the preferred upper limits may also be lower than 99% by weight, for example 80% by weight, 70% by weight or even 25% by weight.

The present invention is to be additionally elucidated in detail hereinafter by examples.

EXAMPLES

The percentages which follow, unless stated otherwise, are percentages by weight.

(I) Synthesis of the Rheology Control Agents

COMPARATIVE EXAMPLES

Comparative Example 1 (Analogous to Example 12 of DE-A1-19919482)

Firstly, a monoadduct is prepared according to patent specification EP 1188779 from tolylene 2,4-diisocyanate (Desmodur T100, Bayer) and lauryl alcohol. In a reaction vessel, 1.65 g (0.04 mol) of LiCl are dissolved in 75.0 g of N-ethylpyrrolidone (BASF) while stirring. Thereafter, 3.55 g (0.026 mol) of meta-xylylenediamine are added and the clear mixture is heated to 60° C. Subsequently, 19.8 g (0.052 mol) of the monoadduct of Desmodur T100 and lauryl alcohol are added dropwise while stirring within 1 hour, such that the temperature does not rise above 80° C. To complete the reaction, the reaction mixture is stirred at 80° C. for 3 hours. A clear, colorless and fluid product with a 25% content of urea urethane is obtained.

Comparative Example 2

Firstly, a monoadduct is prepared according to patent specification EP 1188779 from tolylene 2,4-diisocyanate (Desmodur T100, Bayer) and lauryl alcohol. In a reaction vessel, 1.65 g (0.04 mol) of LiCl are dissolved in 75.0 g of methyl 5-(dimethylamino)-2-methyl-5-oxopentanoate while stirring. Thereafter, 3.55 g (0.026 mol) of meta-xylylenediamine are added and the clear mixture is heated to 60° C. Subsequently, 19.8 g (0.052 mol) of the monoadduct of Desmodur T100 and lauryl alcohol are added dropwise while stirring within 1 hour, such that the temperature does not rise above 80° C. To complete the reaction, the reaction mixture is stirred at 80° C. for 3 hours. A clear, colorless and fluid product with a 25% content of urea urethane is obtained.

Comparative Example 3

As comparative example 3, example 5 from EP 2292675 A1 was prepared.

EXAMPLES

Firstly, as synthons for the syntheses of the urea urethanes described further down, the following monoadducts are prepared according to patent specification EP 1188779:

Monoadduct 1 is prepared from a mixture of tolylene 2,4-diisocyanate and tolylene 2,6-diisocyanate (Desmodur T65, Bayer) and (Z)-octadec-9-enol (oleyl alcohol, Merck).

Monoadduct 2 is prepared from a mixture of tolylene 2,4-diisocyanate and tolylene 2,6-diisocyanate (Desmodur T65, Bayer) and Exxal™ 13 Tridecyl Alcohol ($C_{13}$-rich, $C_{11-14}$-alkanol; Exxon Mobil Corporation).

Monoadduct 3 is prepared from tolylene 2,4-diisocyanate (Desmodur T100, Bayer) and 1-dodecanol (Aldrich).

Example 1

In a reaction vessel with a stirrer, dropping funnel and nitrogen inlet, 3.0 g (0.07 mol) of LiCl are dissolved in 150.0 g of N-methylpyrrolidone (BASF) while stirring. Thereafter, 6.5 g (0.047 mol) of meta-xylylenediamine are added and the mixture is heated to 60° C. Subsequently, a mixture of 24.3 g of monoadduct 1 (0.052 mol) and 16.2 g of monoadduct 2 (0.042 mol) is added dropwise while stirring within 1 hour at such a rate that the temperature does not rise above 80° C. To complete the reaction, the reaction mixture, after the addition has ended, is stirred at 80° C. for 3 hours. A clear, colorless and fluid product is obtained. The product contains a 25% content of urea urethane.

Example 2

In a reaction vessel with a stirrer, dropping funnel and nitrogen inlet, 3.3 g (0.078 mol) of LiCl are dissolved in 90.0 g of N-octylpyrrolidone (BASF) while stirring. Thereafter, 7.2 g (0.052 mol) of meta-xylylenediamine are added and the mixture is heated to 60° C. Subsequently, 49.5 g (0.104 mol) of monoadduct 1 are added dropwise while stirring within 1 hour, such that the temperature does not rise above 80° C. To complete the reaction, the reaction mixture is stirred at 80° C. for 3 hours. A clear, colorless and fluid product is obtained. The product contains a 40% content of urea urethane.

Example 3

In a reaction vessel with a stirrer, dropping funnel and nitrogen inlet, 2.8 g (0.066 mol) of LiCl are dissolved in 150.0 g of N-octylpyrrolidone (BASF) while stirring. Thereafter, 6.0 g (0.044 mol) of meta-xylylenediamine are added and the mixture is heated to 60° C. Subsequently, 41.2 g (0.088 mol) of monoadduct 1 are added dropwise while stirring within 1 hour, such that the temperature does not rise above 80° C. To complete the reaction, the reaction mixture is stirred at 80° C. for 3 hours. A clear, colorless and fluid product is obtained. The product contains a 25% content of urea urethane.

Example 4

In a reaction vessel with a stirrer, dropping funnel and nitrogen inlet, 2.8 g (0.066 mol) of LiCl are dissolved in 150.0 g of N-methylpyrrolidone (BASF) while stirring. Thereafter, 6.0 g (0.044 mol) of meta-xylylenediamine are added and the mixture is heated to 60° C. Subsequently, 41.2 g (0.088 mol) of monoadduct 1 are added dropwise while stirring within 1 hour, such that the temperature does not rise above 80° C. To complete the reaction, the reaction mixture is stirred at 80° C. for 3 hours. A clear, colorless and fluid product is obtained. The product contains a 25% content of urea urethane.

Example 5

In a reaction vessel with a stirrer, dropping funnel and nitrogen inlet, 4.5 g (0.105 mol) of LiCl are dissolved in 225.0 g of N-octylpyrrolidone (BASF) while stirring. Thereafter, 9.7 g (0.07 mol) of meta-xylylenediamine are added and the mixture is heated to 60° C. Subsequently, a mixture of 36.5 g (0.077 mol) of monoadduct 1 and 24.4 g (0.063 mol) of monoadduct 2 is added dropwise while stirring within 1 hour, such that the temperature does not rise above 80° C. To complete the reaction, the reaction mixture is stirred at 80° C. for 3 hours. A clear, colorless and fluid product is obtained. The product contains a 25% content of urea urethane.

Example 6

In a reaction vessel with a stirrer, dropping funnel and nitrogen inlet, 5.4 g (0.127 mol) of LiCl are dissolved in 210.0 g of dimethyl sulfoxide (DMSO, Merck) while stirring. Thereafter, 11.7 g (0.085 mol) of meta-xylylenediamine are added and the mixture is heated to 60° C. Subsequently, a mixture of 42.0 g (0.089 mol) of monoadduct 1 and 31.0 g (0.081 mol) of monoadduct 2 is added dropwise while stirring within 1 hour, such that the temperature does not rise above 80° C. To complete the reaction, the reaction mixture is stirred at 80° C. for 3 hours. A clear, colorless and fluid product is obtained. The product contains a 30% content of urea urethane.

Example 7

In a reaction vessel with a stirrer, dropping funnel and nitrogen inlet, 5.3 g (0.126 mol) of LiCl are dissolved in 210.0 g of dimethyl sulfoxide (DMSO, Merck) while stirring. Thereafter, 11.6 g (0.084 mol) of meta-xylylenediamine are added and the mixture is heated to 60° C. Subsequently, a mixture of 45.6 g (0.097 mol) of monoadduct 1 and 27.5 g (0.071 mol) of monoadduct 2 is added dropwise while stirring within 1 hour, such that the temperature does not rise above 80° C. To complete the reaction, the reaction mixture is stirred at 80° C. for 3 hours. A clear, colorless and fluid product is obtained. The product contains a 30% content of urea urethane.

Example 8

In a reaction vessel with a stirrer, dropping funnel and nitrogen inlet, 6.3 g (0.149 mol) of LiCl are dissolved in 195.0 g of dimethyl sulfoxide (DMSO, Merck) while stirring. Thereafter, 13.7 g (0.099 mol) of meta-xylylenediamine are added and the mixture is heated to 60° C. Subsequently, a mixture of 46.8 g (0.099 mol) of monoadduct 1 and 38.2 g (0.099 mol) of monoadduct 2 is added dropwise while stirring within 1 hour, such that the temperature does not rise above 80° C. To complete the reaction, the reaction mixture is stirred at 80° C. for 3 hours. A clear, colorless and fluid product is obtained. The product contains a 35% content of urea urethane.

Example 9

In a reaction vessel with a stirrer, dropping funnel and nitrogen inlet, 6.3 g (0.149 mol) of LiCl are dissolved in 195.0 g of dimethyl sulfoxide (DMSO, Merck) while stirring. Thereafter, 13.5 g (0.098 mol) of meta-xylylenediamine are added and the mixture is heated to 60° C. Subsequently, a mixture of 51.1 g (0.108 mol) of monoadduct 1 and 34.1 g (0.089 mol) of monoadduct 2 is added dropwise while stirring within 1 hour, such that the temperature does not rise above 80° C. To complete the reaction, the reaction mixture is stirred at 80° C. for 3 hours. A clear, colorless and fluid product is obtained. The product contains a 35% content of urea urethane.

Example 10

In a reaction vessel with a stirrer, dropping funnel and nitrogen inlet, 6.2 g (0.146 mol) of LiCl are dissolved in 195.0 g of dimethyl sulfoxide (DMSO, Merck) while stirring. Thereafter, 13.4 g (0.098 mol) of meta-xylylenediamine are added and the mixture is heated to 60° C. Subsequently, a mixture of 55.3 g (0.117 mol) of monoadduct 1 and 30.1 g (0.078 mol) of monoadduct 2 is added dropwise while stirring within 1 hour, such that the temperature does not rise above 80° C. To complete the reaction, the reaction mixture is stirred at 80° C. for 3 hours. A clear, colorless and fluid product is obtained. The product contains a 35% content of urea urethane.

Example 11

In a reaction vessel with a stirrer, dropping funnel and nitrogen inlet, 6.3 g (0.149 mol) of LiCl are dissolved in 245.0 g of dimethyl sulfoxide (DMSO, Merck) while stirring. Thereafter, 13.7 g (0.099 mol) of meta-xylylenediamine are added and the mixture is heated to 60° C. Subsequently, a mixture of 46.8 g (0.099 mol) of monoadduct 1 and 38.2 g (0.099 mol) of monoadduct 2 is added dropwise while stirring within 1 hour, such that the temperature does not rise above 80° C. To complete the reaction, the reaction mixture is stirred at 80° C. for 3 hours. A clear, colorless and fluid product is obtained. The product contains a 30% content of urea urethane.

Example 12

In a reaction vessel with a stirrer, dropping funnel and nitrogen inlet, 6.3 g (0.149 mol) of LiCl are dissolved in 280.0 g of dimethyl sulfoxide (DMSO, Merck) while stirring. Thereafter, 13.7 g (0.099 mol) of meta-xylylenediamine are added and the mixture is heated to 60° C. Subsequently, a mixture of 46.8 g (0.099 mol) of monoadduct 1 and 38.2 g (0.099 mol) of monoadduct 2 is added dropwise while stirring within 1 hour, such that the temperature does not rise above 80° C. To complete the reaction, the reaction mixture is stirred at 80° C. for 3 hours. A clear, colorless and fluid product is obtained. The product contains a 27.5% content of urea urethane.

Example 13

In a reaction vessel with a stirrer, dropping funnel and nitrogen inlet, 6.3 g (0.149 mol) of LiCl are dissolved in 280.0 g of dimethyl sulfoxide (DMSO, Merck) while stirring. Thereafter, 13.5 g (0.098 mol) of meta-xylylenediamine are added and the mixture is heated to 60° C. Subsequently, a mixture of 51.1 g (0.108 mol) of monoadduct 1 and 34.1 g (0.089 mol) of monoadduct 2 is added dropwise while stirring within 1 hour, such that the temperature does not rise above 80° C. To complete the reaction, the reaction mixture is stirred at 80° C. for 3 hours. A clear, colorless and fluid product is obtained. The product contains a 27.5% content of urea urethane.

Example 14

In a reaction vessel with a stirrer, dropping funnel and nitrogen inlet, 6.2 g (0.146 mol) of LiCl are dissolved in 280.0 g of dimethyl sulfoxide (DMSO, Merck) while stirring. Thereafter, 13.4 g (0.098 mol) of meta-xylylenediamine are added and the mixture is heated to 60° C. Subsequently, a mixture of 55.3 g (0.117 mol) of monoadduct 1 and 30.1 g (0.078 mol) of monoadduct 2 is added dropwise while stirring within 1 hour, such that the temperature does not rise above 80° C. To complete the reaction, the reaction mixture is stirred at 80° C. for 3 hours. A clear, colorless and fluid product is obtained. The product contains a 27.5% content of urea urethane.

Example 15

In a reaction vessel with a stirrer, dropping funnel and nitrogen inlet, 4.2 g (0.099 mol) of LiCl are dissolved in 130.0 g of N-octylpyrrolidone (BASF) at 60° C. while stirring. Thereafter, 9.1 g (0.066 mol) of meta-xylylenediamine are added, and the solution turns cloudy after a few seconds. Subsequently, a mixture of 32.1 g of monoadduct 1 (0.066 mol) and 25.5 g of monoadduct 3 (0.066 mol) is added dropwise while stirring within 30 minutes at such a rate that the temperature does not rise above 80° C. During this time, the reaction mixture turns completely clear. To complete the reaction, the reaction mixture, after the addition has ended, is stirred at 80° C. for 3 hours. A clear, yellowish and fluid product is obtained. The product contains 35% urea urethane.

Example 16

In a reaction vessel with a stirrer, dropping funnel and nitrogen inlet, 4.0 g (0.095 mol) of LiCl are dissolved in 130.0 g of N-octylpyrrolidone (BASF) at 60° C. while stirring. Thereafter, 8.7 g (0.064 mol) of meta-xylylenediamine are added, and the solution turns cloudy after a few seconds. Subsequently, a mixture of 45.0 g of monoadduct 1 (0.095 mol) and 12.2 g of monoadduct 3 (0.032 mol) is added dropwise while stirring within 30 minutes at such a rate that the temperature does not rise above 80° C. During this time, the reaction mixture turns completely clear. To complete the reaction, the reaction mixture, after the addition has ended, is stirred at 80° C. for 3 hours. A clear, yellowish and fluid product is obtained. The product contains 35% urea urethane.

Example 17 (Oligomer/Polymer; $M_n$=3135, $M_w$=3708)

In a reaction vessel with a stirrer, dropping funnel and nitrogen inlet, 6.0 g (0.142 mol) of LiCl are dissolved in 130.0 g of N-octylpyrrolidone (BASF) at 60° C. while stirring. Thereafter, 9.7 g (0.071 mol) of meta-xylylenediamine are added, and the solution turns cloudy after a few seconds. Subsequently, a mixture of 51.4 g of monoadduct 1 (0.109 mol) and 2.8 g of tolylene diisocyanate (0.016 mol) (Desmodur T80; mixture of tolylene 2,4-diisocyanate and tolylene 2,6-diisocyanate from Bayer) is added dropwise while stirring within 30 minutes at such a rate that the temperature does not rise above 80° C. During this time, the reaction mixture turns completely clear. To complete the reaction, the reaction mixture, after the addition has ended, is stirred at 80° C. for 3 hours. A clear, yellowish and fluid product is obtained. The product contains 35% urea urethane.

Example 18 (Oligomer/Polymer; $M_n$=3317, $M_w$=3967)

In a reaction vessel with a stirrer, dropping funnel and nitrogen inlet, 6.2 g (0.147 mol) of LiCl are dissolved in 130.0 g of N-octylpyrrolidone (Aldrich) while stirring. Thereafter, 10.0 g (0.073 mol) of meta-xylylenediamine are added and the mixture is heated to 60° C. Subsequently, a mixture of 50.1 g (0.105 mol) of monoadduct 1 and 3.6 g (0.021 mol) of tolylene diisocyanate (isomer mixture of tolylene 2,4/2,6-diisocyanate in a ratio of 4:1 from Bayer; Desmodur T80) is added dropwise while stirring within 35 minutes, such that the temperature does not rise above 80° C. To complete the reaction, the reaction mixture is stirred at 80° C. for 3 hours and at 90° C. for another 30 minutes. A clear, yellow and fluid product is obtained. The product contains a 35% content of urea urethane.

Example 19 (Oligomer/Polymer; $M_n$=3377, $M_w$=4102)

In a reaction vessel with a stirrer, dropping funnel and nitrogen inlet, 6.5 g (0.153 mol) of LiCl are dissolved in 130.0 g of N-octylpyrrolidone (Aldrich) while stirring. Thereafter, 10.4 g (0.077 mol) of meta-xylylenediamine are added and the mixture is heated to 60° C. Subsequently, a mixture of 48.7 g (0.102 mol) of monoadduct 1 and 4.4 g (0.026 mol) of tolylene diisocyanate (isomer mixture of tolylene 2,4/2,6-diisocyanate in a ratio of 4:1 from Bayer; Desmodur T80) is added dropwise while stirring within 35 minutes, such that the temperature does not rise above 80° C. To complete the reaction, the reaction mixture is stirred at 80° C. for 3 hours and at 90° C. for another 30 minutes. A clear, yellow and fluid product is obtained. The product contains a 35% content of urea urethane.

Example 20 (Oligomer/Polymer; $M_n$=5021, $M_w$=7865)

In a reaction vessel with a stirrer, dropping funnel and nitrogen inlet, 4.8 g (0.114 mol) of LiCl are dissolved in 130.0 g of N-octylpyrrolidone (Aldrich) at 60° C. while stirring. Thereafter, 15.5 g (0.114 mol) of meta-xylylenediamine are added, and the solution turns cloudy after a few seconds. Subsequently, a mixture of 36.4 g of monoadduct 1 (0.076 mol) and 13.3 g of tolylene diisocyanate (0.076 mol) (isomer mixture of tolylene 2,4/2,6-diisocyanate in a ratio of 4:1 from Bayer; Desmodur T80) is added dropwise while stirring within 50 minutes at such a rate that the temperature does not rise above 80° C. During this time, the reaction mixture turns almost completely clear. To complete the reaction, the reaction mixture, after the addition has ended, is stirred at 80° C. for 3 hours. Within this time, the solution turns completely clear, and so a clear, yellow and viscous product is obtained. The product contains 35% urea urethane.

Example 21 (Oligomer/Polymer; $M_n$=3935, $M_w$=5512)

In a reaction vessel with a stirrer, dropping funnel and nitrogen inlet, 4.0 g (0.094 mol) of LiCl are dissolved in 130.0 g of N-octylpyrrolidone (Aldrich) at 60° C. while stirring. Thereafter, 12.8 g (0.094 mol) of meta-xylylenediamine are added, and the solution turns cloudy after a few seconds. Subsequently, a mixture of 45.0 g of monoadduct 1 (0.094 mol) and 8.2 g of tolylene diisocyanate (0.047 mol) (isomer mixture of tolylene 2,4/2,6-diisocyanate in a ratio of 4:1 from Bayer; Desmodur T80) is added dropwise while stirring within 50 minutes at such a rate that the temperature does not rise above 80° C. During this time, the reaction mixture turns completely clear. To complete the reaction, the reaction mixture, after the addition has ended, is to stirred at 80° C. for 3 hours. A clear, yellow and viscous product is obtained. The product contains 35% urea urethane.

(II) Performance Testing of the Urea Urethanes Suitable as Rheology Control Agents Raw Materials Used

| Name | Description | Manufacturer |
|---|---|---|
| Acridic A 188 | Nonaqueous dispersion | Dainippon Ink & Chemicals, Inc. |
| Acridic A 1300 | Nonaqueous dispersion | Dainippon Ink & Chemicals, Inc. |
| Bayferrox 130 M | Iron oxide red pigment | Lanxess Deutschland GmbH |
| Blanc Fixe N | Barium sulfate | Sachtleben Chemie GmbH |
| Borchinox M 2 | 2-Butanone oxime | Borchers GmbH |
| BYK-052 | Defoamer | BYK-Chemie GmbH |
| Claytone 3 | Sheet silicate | BYK Chemie GmbH |
| Disperbyk-108 | Wetting and dispersing additive | BYK-Chemie GmbH |
| Dowanol PMA | Propane-1,2-diol monoacetate monomethyl ether | Dow Chemical Company |
| Durcal 5 | Calcium carbonate | Omya |
| Heucophos ZCP - plus | Zinc/calcium/strontium/aluminum orthophosphate silicate hydrate | Heubach GmbH |
| Heucorin RZ | Org. corrosion inhibitor zinc 5-nitroisophthalate | Heubach GmbH |
| Isomerized C1618 Alpha Olefin | Synthetic olefin | Ineos Oligomers |
| Micro Talc AT-1 | Talc magnesite | Mondo Minerals BV |
| Octa Soligen Calcium 10 | Calcium siccative | Borchers GmbH |
| Octa Soligen Cobalt 12 | Cobalt siccative | Borchers GmbH |
| Setal A F 26 X | Short oil alkyd 60% in xylene | Nuplex Resins GmbH |
| Shellsol A | Aromatic hydrocarbon mixture | Overlack AG |
| Testbenzin K 30 | Special boiling point spirit 145-200 | Overlack AG |
| Tioxide TR 92 | Titanium dioxide | Huntsman Pigments |
| Worléekyd B 6301 | Long oil alkyd resin, 90% in dearomat. HC 180-220 | Worlée Chemie GmbH |
| Xylene | Isomer mixture | Overlack AG |

Elucidation of the Rating Scale

| | | |
|---|---|---|
| Gel strength: | 1 | very strong |
| | 2 | strong |
| | 3 | moderate |
| | 4 | very weak |
| | 5 | no gel |
| Cloudiness (compatibility): | 1 | clear |
| | 2 | slightly cloudy |
| | 3 | cloudy |
| | 4 | very cloudy |
| | 5 | extremely cloudy |

Test System 1: Solvent Mixtures

A 100 mL glass bottle is charged with 50 g of the respective solvent mixture consisting of xylene/n-butanol 90:10 (w/w) and Dowanol PMA/Shellsol A/isobutanol 50:25:25 (w/w/w), and then the respective additive is incorporated while stirring by Dispermat CV (toothed disk d=2.5 cm at 1000 rpm). In all cases, a dosage corresponding to 2% of the urea urethane (based on the total mass of the solvent mixture) was chosen. On completion of addition, stirring is continued for another 1 minute.

Subsequently, the samples are left to stand at room temperature for 1 day and then the gel strength is assessed visually as a measure of the rheological efficacy, and the compatibility of the additive in the system is assessed by the cloudiness.

| | Xylene/n-butanol 90:10 | | Dowanol MPA/Shellsol A/isobutanol 50:25:25 | |
|---|---|---|---|---|
| Product | Gel strength | Cloudiness | Gel strength | Cloudiness |
| Blank sample without additive | 5 | 1 | 5 | 1 |
| Comparative example 1 | 4 | 3 | 5 | 4 |
| Example 1 | 2 | 2 | 3 | 3 |
| Example 2 | 3 | 1 | 3 | 1 |

It is apparent from the table that comparative example 1 gives a significantly poorer gel strength and is less compatible than inventive examples 1 and 2.

Test System 2: Acrydic A-188/A-1300 White Paint

A 100 mL glass bottle is charged with 50 g of Acrydic A-188/A-1300 white paint according to the composition specified below, and then the respective additive is incorporated while stirring by Dispermat CV (toothed disk d=2.5 cm at 1000 rpm). On completion of addition, stirring is continued for another 1 minute. In all cases, a dosage corresponding to 0.25% by weight of the urea urethane (based on the total mass of the formulation) was chosen.

Subsequently, the samples are left to stand at room temperature for 1 day and then the testing of the sag resistance as a measure of the rheological efficacy was conducted under application conditions.

For this purpose, the sample is mixed homogeneously by spatula and then applied to contrast charts with a 50-500 μm step gap bar applicator and an automatic applicator bench (from BYK-Gardner) at a speed of 5 cm/s. After the application, the contrast charts are directly suspended horizontally for drying. After the drying, the maximum layer thickness in μm (wet) at which the paint does not sag, meaning that no runs or blister formation are apparent, is determined. The higher the value for the sag resistance with use of equal amounts of urea urethane, the better the rheological efficacy.

Formulation of the White Paint:

| Acrydic A-188/A-1300 white paint | |
|---|---|
| Acridic A 188 | 12.7 |
| Tioxide TR 92 | 22.0 |
| Disperbyk 108 | 2.5 |
| Testbenzin K 30 | 12.5 |
| Dispermat, 40° C., 30 min, 8500 rpm, 4 cm toothed disk | |
| Acridic A 1300 | 44.0 |
| Testbenzin K 30 | 6.3 |
| | 100.0 |

Results:

| Product | Sag resistance μm (wet) |
| --- | --- |
| Blank sample without additive | 100 |
| Comparative example 2 | 150 |
| Example 3 | 200 |
| Example 4 | 200 |

It is apparent in the table that comparative example 2 exhibits poorer rheological efficacy in the form of sag resistance than inventive examples 3 and 4.

Test System 3: Setal A F 26 X White Paint

A 100 mL glass bottle is charged with 50 g of Setal A F 26 X white paint according to the composition specified below, and then the respective additive is incorporated while stirring by Dispermat CV (toothed disk d=2.5 cm at 1000 rpm). In all cases, a dosage corresponding to 0.5% by weight of the urea urethane (based on the total mass of the paint formulation) was chosen. On completion of addition, stirring is continued for another 1 minute.

Subsequently, the samples are left to stand at room temperature for 1 day and the sag resistance is assessed by application as a measure of the rheological efficacy. For this purpose, the sample is mixed homogeneously by spatula and then applied to contrast charts with a 50-500 μm step gap bar applicator and an automatic applicator bench (from BYK-Gardner) at a speed of 5 cm/s. After the application, the contrast charts are directly suspended horizontally for drying. After the drying, the maximum layer thickness in μm (wet) at which the paint does not sag, meaning that no runs or blister formation are apparent, is determined. The higher the value for the sag resistance with use of equal amounts of the urea urethane, the better the rheological efficacy.

Formulation of the Setal White Paint:

| | |
| --- | --- |
| Setal A F 26 X | 34.5 |
| Shellsol A | 7.8 |
| Emulsifying aid* | 0.2 |
| BYK-052 | 0.2 |
| Bayferrox 130 M | 6.0 |
| Micro Talc AT-1 | 7.0 |
| Heucophos ZCP - plus | 21.0 |
| Heucorin RZ | 0.5 |
| Dispermat, 40° C., 30 min, 8500 rpm, 4 cm toothed disk | |
| Setal A F 26 X | 8.0 |
| Shellsol A | 14.2 |
| Calcium 10 | 0.3 |
| Cobalt 12 | 0.2 |
| Borchinox M 2 | 0.1 |
| | 100.0 |

*available from BYK Chemie GmbH

Results

| Product | Sag resistance μm (wet) |
| --- | --- |
| Blank sample without additive | 50 |
| Comparative example 2 | 100 |
| Example 1 | 200 |
| Example 3 | 200 |
| Example 5 | 200 |

It is apparent from the table that comparative example 2 enables poorer sag resistance than the products of the invention.

Test System 4: Worleekyd B6301 Binder

A 100 mL glass bottle is charged with 50 g of Worleekyd B6301 binder, and then the respective additive is incorporated while stirring by Dispermat CV (toothed disk d=2.5 cm at 1000 rpm). In all cases, a dosage corresponding to 1.0% by weight of the urea urethane (based on the total mass of the paint formulation) was chosen. On completion of addition, stirring is continued for another 1 minute.

Subsequently, the samples are left to stand at room temperature for 1 day and the sag resistance is assessed by application as a measure of the rheological efficacy. For this purpose, the sample is mixed homogeneously by spatula and then applied to contrast charts with a 50-500 μm step gap bar applicator and an automatic applicator bench (from BYK-Gardner) at a speed of 5 cm/s. After the application, the contrast charts are directly suspended horizontally for drying. After the drying, the maximum layer thickness in μm (wet) at which the paint does not sag, meaning that no runs or blister formation are apparent, is determined. The higher the value for the sag resistance with use of the same active substance, the better the rheological efficacy.

| Product | Sag resistance μm (wet) |
| --- | --- |
| Blank sample without additive | <50 |
| Comparative example 1 | 50 |
| Comparative example 2 | 100 |
| Example 6 | 500 |
| Example 7 | 500 |
| Example 8 | 600 |
| Example 9 | 550 |
| Example 10 | 550 |
| Example 11 | 350 |
| Example 12 | 350 |
| Example 13 | 400 |
| Example 14 | 350 |

It is apparent from the table that comparative examples 1 and 2 enable poorer sag resistance than the inventive examples.

Test System 5: Oil-Based Drilling Mud

Firstly, 400 g of drilling mud are produced according to the formulation specified by means of a Hamilton Beach mixer, GM20 type, HMD200-CE model (manufacturer: Hamilton Beach; setting: level 1).

The mud is divided into 100 g samples and the respective additive is incorporated with an Ultra-Turrax stirrer (manufacturer: IKA-Werke GmbH, model T 45) at 6000 rpm for 5 min (the blank sample is sheared analogously). In all cases, a dosage corresponding to 0.5% by weight of the urea urethane (based on the total mass of the drilling mud) was chosen.

For the separation characteristics, 60 g of drilling mud in each case were dispensed into 50 mL snap-lid bottles and stored at room temperature for 4 weeks. Thereafter, the separation (syneresis formation) in % is evaluated, based on the total fill height in the snap-lid bottle, as a measure of the rheological efficacy. The lower the height of the separated phase, the better the rheological efficacy of the additive and the better it can consequently be used to counter the separation of the components.

For selected examples, the remaining 40 g of the drilling mud are dispensed into 50 mL glass bottles. After standing at RT for 16 h, the viscosity is measured in a temperature-dependent manner by Physica MCR-301 rheometer (manufacturer: Anton Paar GmbH) at the three temperatures of 4° C., 25° C. and 66° C. under shear rate control at the shear rates of 10, 150, 300, 500 and 1000 l/s with a DPP30 plate-plate geometry and a 0.5 mm measurement gap.

Oil-Based Drilling Mud:

| Component | Weight/g | Mixing/min |
|---|---|---|
| Isomerized C1618 Alpha Olefin | 25.0 | |
| Claytone 3 | 0.2 | 10 |
| Durcal 5 | 0.5 | 10 |
| Emulsifying aid* | 1.8 | 10 |
| CaCl$_2$ solution, 25% in water | 18.5 | 10 |
| Blanc Fixe N | 54.0 | 10 |
| | 100.0 | |

*available from BYK Chemie GmbH

Results: Separation

| Product | Dosage, % by wt. of urea urethane | Separation (syneresis) % after 4 weeks at RT |
|---|---|---|
| Blank sample without additive | — | 36 |
| Comparative example 1 | 0.5 | 27 |
| Comparative example 3 | 0.5 | 44 |
| Example 2 | 0.5 | 9 |
| Example 15 | 0.5 | 4 |
| Example 16 | 0.5 | 3 |
| Example 17 | 0.5 | 1 |
| Example 18 | 0.5 | 1 |
| Example 19 | 0.5 | 1 |
| Example 20 | 0.5 | 4 |
| Example 21 | 0.5 | 2 |

It is apparent from the table that the products of the invention according to examples 2 and 15 to 21 are able to better stabilize the system again separation than comparative examples 1 and 3 or the blank sample.

Results: Viscosity Measurement

| Product | Temperature/° C. | Viscosity/mPas at shear rate 1/s | | | | |
|---|---|---|---|---|---|---|
| | | 10 | 150 | 300 | 500 | 1000 |
| Blank sample without additive | 4.4 | 797 | 178 | 133 | 114 | 92 |
| | 25 | 272 | 79 | 62 | 55 | 46 |
| | 66 | 62 | 19 | 16 | 14 | 12 |
| Comparative example 1 | 4.4 | 831 | 218 | 171 | 152 | 130 |
| | 25 | 305 | 101 | 83 | 76 | 67 |
| | 66 | 183 | 49 | 39 | 34 | 28 |
| Example 2 | 4.4 | 2953 | 460 | 308 | 247 | 182 |
| | 25 | 1987 | 289 | 189 | 149 | 108 |
| | 66 | 1176 | 177 | 117 | 100 | 73 |

It is apparent from the table that comparative example 1 enables only a smaller increase in viscosity compared to the inventive product from example 2.

The invention claimed is:

1. A urea urethane of the general formula (I)

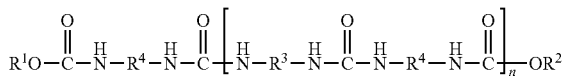

(I)

in which
R$^1$ is a mono- or polyunsaturated, branched or unbranched alkenyl radical having 12 to 24 carbon atoms,
R$^2$ is a saturated branched or unbranched alkyl radical having 8 to 24 carbon atoms or a mono- or polyunsaturated, branched or unbranched alkenyl radical having 12 to 24 carbon atoms, a mono- or polyunsaturated, branched or unbranched alkynyl radical having 12 to 24 carbon atoms or a polyunsaturated hydrocarbyl radical which has 12 to 24 carbon atoms and has at least one carbon-carbon double bond and at least one carbon-carbon triple bond,
wherein the proportion by weight of the urea urethanes of the formula (I) in which both R$^1$ and R$^2$ radicals are unsaturated is 10% to 100%, based on the totality of the urea urethanes of the formula (I), and
the proportion by weight of the urea urethanes of the formula (I) in which only the R$^1$ radical is unsaturated is 0% to 90%, based on the totality of the urea urethanes of the formula (I),
and
all n R$^3$ radicals are independently one or more radicals selected from the structural units (IIa-o), (IIa-m), (IIa-p), (IIb-o), (IIb-m) and (IIb-p)

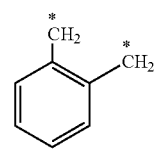

(IIa-o)

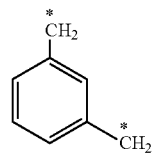

(IIa-m)

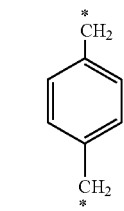

(IIa-p)

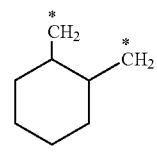

(IIb-o)

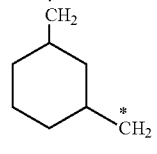

(IIb-m)

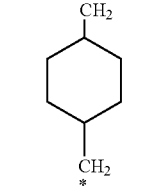

(IIb-p)

and
all n+1 R⁴ radicals are independently one or more radicals selected from the structural units (IIIa), (IIIb), (IIIc), (IIId), (IIIe), (IIIf), (IIIg) and (IIIh)

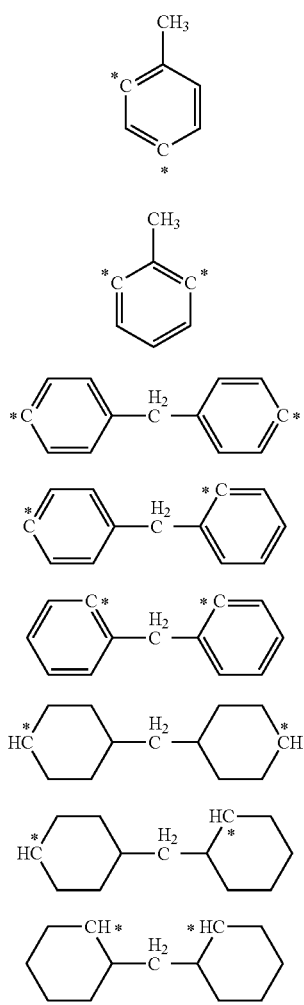

and
n is an integer ≥1, where the upper limit for n arises from the maximum number-average molecular weight $M_n$ of the urea urethanes of the general formula (I) which is 65,000 g/mol and which is determined by means of gel permeation chromatography to DIN 55672-2 using a polymethylmethacrylate standard, and
where the bonding sites of the R³ and R⁴ radicals to the adjacent NH groups in the structural units formulae are indicated by the * symbol.

2. The urea urethane as claimed in claim 1, characterized in that
the R¹ radical is a monounsaturated alkenyl radical having 16 to 20 carbon atoms,
the R² radical is a saturated branched alkyl radical having 10 to 16 carbon atoms or a monounsaturated alkenyl radical having 16 to 20 carbon atoms,
the n R³ radicals are independently one or more radicals selected from the structural units (IIa-m) and (IIa-p), and
the n+1 R⁴ radicals are independently one or more radicals of the structural units (IIIa) and (IIIb).

3. The urea urethane as claimed in claim 1, characterized in that
the R¹ radical is an unbranched octadecenyl radical,
the R² radical is a branched or unbranched $C_{10}$-$C_{14}$-alkyl radical or an unbranched octadecenyl radical,
the n R³ radicals are a radical of the structural unit (IIa-m), and
the n+1 R⁴ radicals are independently one or more radicals of the structural units (IIIa) and (IIIb).

4. The urea urethane as claimed in claim 1, characterized in that the structural units (IIIa) and (IIIb) are present in the n+1 R⁴ radicals in a molar ratio of 40:60 up to a molar ratio of 100:0.

5. The urea urethane as claimed in claim 1, characterized in that R¹ and R² are a mono- or polyunsaturated, branched or unbranched alkenyl radical having 16 to 20 carbon atoms.

6. The urea urethane as claimed in claim 1, characterized in that R¹ is oleyl.

7. The urea urethane as claimed in claim 1, characterized in that R¹=R².

8. A urea urethane composition comprising one or more urea urethanes of claim 1.

9. The urea urethane composition as claimed in claim 8, characterized in that it is in liquid form.

10. The urea urethane composition as claimed in claim 8, wherein the urea urethane(s) is/are dissolved in a polar aprotic solvent.

11. The urea urethane composition as claimed in claim 10, wherein the polar aprotic solvent is selected from the group consisting of substituted N-alkylpyrrolidones, unsubstituted N-alkylpyrrolidones, dialkyl sulfoxides, substituted amides, unsubstituted amides and organic salts having a melting point of ≤80° C.

12. A process for preparing the urea urethane compositions as claimed in claim 8, characterized in that,
in the presence of a polar aprotic solvent,
(a) one or more monoadducts of the formula R¹—O—(CO)—NH—R⁴—NCO or of the formula R²—O—(CO)—NH—R⁴—NCO are prepared from one or more monoalcohols of the formula R¹OH or R²OH, or the formulae R¹OH and R²OH, and one or more diisocyanates of the formula OCN—R⁴—NCO and said monoadduct(s) is/are then reacted
(i) with one or more diamines of the formula H₂N—R³—NH₂ or
(ii) with one or more prepolymers, NH₂-terminated at both ends, of one or more diamines of the formula H₂N—R³—NH₂ and one or more diisocyanates of the formula OCN—R⁴—NCO or
(iii) with one or more diamines of the formula H₂N—R³—NH₂ and one or more diisocyanates of the formula OCN—R⁴—NCO or
(iv) with one or more prepolymers NH₂-terminated at both ends or a mixture of one or more diamines of the structure H₂N—R³—NH₂ and one or more prepolymers NH₂-terminated at both ends, and one or more diisocyanates of the formula OCN—R⁴—NCO;
or
(b) one or more prepolymers, NCO-terminated at both ends, of one or more diisocyanates of the formula OCN—R⁴—NCO and one or more diamines of the formula H₂N—R³—NH₂ is/are prepared, and the prepolymer(s) is/are reacted with one or more monoalcohols of the formulae R¹OH or R²OH, or the formulae R¹OH and R²OH;

and
wherein at least one monoalcohol of the formula $R^1OH$ is used in process variants (a) and (b).

13. A process for preparing a urea urethane of formula (I) as defined in claim 1, characterized in that
in the presence of a polar aprotic solvent,
(a) one or more monoadducts of the formula $R^1$—O—(CO)—NH—$R^4$—NCO or of the formula $R^2$—O—(CO)—NH—$R^4$—NCO are prepared from one or more monoalcohols of the formula $R^1OH$ or $R^2OH$, or the formulae $R^1OH$ and $R^2OH$, and one or more diisocyanates of the formula OCN—$R^4$—NCO and said monoadduct(s) is/are then reacted
(i) with one or more diamines of the formula $H_2N$—$R^3$—$NH_2$ or
(ii) with one or more prepolymers, $NH_2$-terminated at both ends, of one or more diamines of the formula $H_2N$—$R^3$—$NH_2$ and one or more diisocyanates of the formula OCN—$R^4$—NCO or
(iii) with one or more diamines of the formula $H_2N$—$R^3$—$NH_2$ and one or more diisocyanates of the formula OCN—$R^4$—NCO or
(iv) with one or more prepolymers $NH_2$-terminated at both ends or a mixture of one or more diamines of the structure $H_2N$—$R^3$—$NH_2$ and one or more prepolymers $NH_2$-terminated at both ends, and one or more diisocyanates of the formula OCN—$R^4$—NCO;
or
(b) one or more prepolymers, NCO-terminated at both ends, of one or more diisocyanates of the formula OCN—$R^4$—NCO and one or more diamines of the formula $H_2N$—$R^3$—$NH_2$ is/are prepared, and the prepolymer(s) is/are reacted with one or more monoalcohols of the formulae $R^1OH$ or $R^2OH$, or the formulae $R^1OH$ and $R^2OH$;
and then the polar aprotic solvent is removed;
and
wherein at least one monoalcohol of the formula $R^1OH$ is used in process variants (a) and (b).

14. A rheology control agent or antisettling agent, characterized in that it comprises one or more urea urethanes of formula (I) as defined in claim 1.

15. A liquid formulation selected from the group consisting of coating compositions, polymer formulations, pigment pastes, sealant formulations, cosmetics, ceramic formulations, drilling fluid solutions, nonaqueous slurries, adhesive formulations, potting compounds, building material formulations, lubricants, spackling compounds, cleaning compositions, printing inks and other inks, characterized in that they comprise one or more urea urethanes of formula (I) as defined in claim 1.

16. The liquid formulation as claimed in claim 15, wherein the proportion of the urea urethane of formula (I) or of the urea urethanes of formula (I) in the overall liquid formulation is 0.1% to 5% by weight.

17. The liquid formulation as claimed in claim 15, characterized in that at least one hydrocarbon selected from the group of the aliphatic, cycloaliphatic, aromatic and araliphatic hydrocarbons is additionally present in the liquid formulation.

18. The liquid formulation as claimed in claim 17, wherein the at least one hydrocarbon is present in the liquid formulation to an extent of at least 10% by weight based on the total weight of the liquid formulation.

19. A rheology control agent or antisettling agent, characterized in that it comprises one or more urea urethane compositions as defined in claim 8.

20. A liquid formulation selected from the group consisting of coating compositions, polymer formulations, pigment pastes, sealant formulations, cosmetics, ceramic formulations, drilling fluid solutions, nonaqueous slurries, adhesive formulations, potting compounds, building material formulations, lubricants, spackling compounds, cleaning compositions, printing inks and other inks, characterized in that they comprise one or more urea urethanes compositions as defined in claim 8.

21. The urea urethane as claimed in claim 1, characterized in that n is an integer from 1 to 5.

* * * * *